US007870284B2

(12) United States Patent
Hunt et al.

(10) Patent No.: US 7,870,284 B2
(45) Date of Patent: Jan. 11, 2011

(54) SCALABLE ARCHITECTURE FOR MAXIMIZING SLIDE THROUGHPUT (75) Inventors: Barry Hunt, Andover, MA (US); Daniel Geagon, Groton, MA (US)

(73) Assignee: Cytyc Corporation, Marlborough, MA (US)

( * ) Notice: Subject to any disclaimer, the term of this patent is extended or adjusted under 35 U.S.C. 154(b) by 1048 days.

(21) Appl. No.: 11/617,112

(22) Filed: Dec. 28, 2006

(65) Prior Publication Data
US 2007/0156917 A1 Jul. 5, 2007

Related U.S. Application Data (60) Provisional application No. 60/755,629, filed on Dec. 29, 2005.

(51) Int. Cl.
*G06F 15/16* (2006.01)
(52) U.S. Cl. ...................... 709/232; 382/128
(58) Field of Classification Search ................ 709/232; 382/128
See application file for complete search history.

(56) References Cited

U.S. PATENT DOCUMENTS

| 6,621,918 | B1 * | 9/2003 | Hu et al. ............... 382/128 |
| 7,039,723 | B2 * | 5/2006 | Hu et al. ............... 709/248 |
| 7,331,925 | B2 * | 2/2008 | McMorrow et al. ...... 600/437 |
| 7,492,970 | B2 * | 2/2009 | Saito et al. ............. 382/305 |
| 7,505,614 | B1 * | 3/2009 | De La Torre-Bueno ..... 382/128 |

FOREIGN PATENT DOCUMENTS

| WO | 03/017833 | 3/2003 |
| WO | 03/021850 | 3/2003 |

OTHER PUBLICATIONS

Montagnat et al., "Medical Images Simulation, Storage, and Processing on the European DataGrid Testbed", Journal Of Grid Computing, Dec. 2004, vol. 2, pp. 387-400. (14 pages).
PCT International Search Report for PCT/US2006/062676, Applicant Cytyc Corp., Forms PCT/ISA/210 and 220, dated Sep. 18, 2007 (4 pages).
PCT Written Opinion of the International Search Authority for PCT/US2006/062676, Applicant Cytyc Corp., Form PCT/ISA/237, dated Sep. 18, 2007 (8 pages).

* cited by examiner

*Primary Examiner*—Bhavesh M Mehta
*Assistant Examiner*—Stephen R Koziol
(74) *Attorney, Agent, or Firm*—Vista IP Law Group LLP (57) ABSTRACT Method and system for imaging and analyzing a biological specimen on a specimen carrier, such as a slide. One or more imagers acquire images of a biological specimen on a slide and generate electronic image data. One or more analysis computers, such as a cluster of analysis computers, are connected to the imagers through a network and process the electronic image data. The number of analysis computers can be different than the number of imagers, and analysis computers can be located remotely from the imagers. The results of processing by the analysis computers are stored to a database, which is accessible by one or more review stations.

29 Claims, 4 Drawing Sheets

SCALABLE ARCHITECTURE FOR MAXIMIZING SLIDE THROUGHPUT

CROSS-REFERENCE TO RELATED APPLICATIONS

This application claims the benefit under 35 U.S.C. §119 to U.S. Provisional Application Ser. No. 60/755,629, filed on Dec. 29, 2005 which is incorporated herein by reference.

FIELD OF THE INVENTION

The field of the present invention generally relates to methods and systems for diagnostically imaging specimens, such as cytological specimens.

BACKGROUND

Known slide processing systems couple an imager comprised of a slide-moving robot, optics, a camera, and a moving stage with a computer. One shortcoming of known slide processing systems is that they are tightly coupled in that for each imager there is an accompanying computer for analyzing the slides. As images are acquired from a given slide, they are analyzed at approximately the same time. When the entire slide has been digitized and all of its images have been analyzed, the slide is removed from the imager stage and the next slide is started.

With sparse slides (i.e., slides with relatively few cells), the computer is able to keep up with the incoming images, and the time it takes to analyze the slide is basically the same as the time it takes the imager to digitize it. However, for dense slides containing many cells or clusters, the computer analysis slows down, thereby causing overall slide processing times to increase, which negatively impacts system throughput.

Further, the computer that controls the imager is the same computer that is used to analyze the digitized images. This common or shared computer configuration places unreasonable constraints on the analysis software, and on the computer upon which it runs. As analysis algorithms are made more sensitive, accurate, and/or sophisticated, they tend to consume more computer resources, which consequently slow them down. Significant engineering effort is expended optimizing these algorithms so that the system throughput is not negatively impacted by more advanced analysis algorithms. Oftentimes, this time-consuming optimization step leads to compromising the image processing algorithm as a result of limited processing resources. In spite of these engineering efforts, in many cases, analysis algorithm improvements are not practical to deploy because they slow down the slide processing too much and negatively impact slide throughput.

It would be desirable, therefore, to have systems and methods that can analyze images more quickly and that can accommodate various processing needs.

SUMMARY

According to one embodiment, a system for imaging and analyzing a biological specimen on a specimen carrier includes at least one imaging computer and at least one analysis computer. The number of analysis computers is different than the number of imaging computers. The at least one imaging computer is configured to acquire images of a biological specimen on a specimen carrier and generate electronic image data from the images. The at least one analysis computer is connected to the at least one imaging computer through a network. The at least one analysis computer is configured to process the electronic image data According to another embodiment, a system for imaging and analyzing a biological specimen on a specimen carrier includes at least one imaging computer, multiple analysis computers, a database and one or more review stations. The number of analysis computers is greater than the number of imaging computers. The at least one imaging computer is configured to acquire images of a biological specimen on a specimen carrier and generate electronic image data from the images. The analysis computers are connected to the at least one imaging computer through a network and are configured to process the electronic image data. The database is configured to store results generated by the analysis computers. A review station is capable of accessing the stored results.

In another embodiment, a method of imaging and analyzing a biological specimen on a specimen carrier includes acquiring images of a biological specimen on a specimen carrier using at least one imaging computer and generating electronic image data from the acquired images. The method further includes transmitting the electronic image data from the at least one imaging computer over a network to at least one analysis computer. The number of analysis computers is different than the number of imaging computers. The electronic image data is processed using the at least one imaging computer.

In accordance with a further alternative embodiment, a method of imaging and analyzing a biological specimen on a specimen carrier includes acquiring images of a biological specimen on a specimen carrier using one or more imaging computers and generating electronic image data from the acquired images. The method further includes transmitting the electronic image data from the one or more imaging computers over a network to one or more of a plurality of analysis computers. The number of analysis computers is greater than the number of imaging computers. The method also includes processing the electronic image data using one or more of the plurality of analysis computers, storing the result of processing the electronic image data to a database and accessing the result stored in the database.

In various embodiments, the network can be a Local Area Network or a Wide Area Network. One or more or all of the analyzer computers can be located remotely from the at least one imaging computer.

Systems and methods can include or involve various numbers of imaging computers and analysis computers, e.g., one imaging computer and a plurality of analysis computers or a plurality of imaging computers and a plurality of analysis computers. In embodiments in which the number of analysis computers is greater than the number of imaging computers, the ratio of the number of analysis computers to the number of acquisition computers can be, for example, at least 3:2.

Systems and methods can include or involve multiple, independent analysis computers. Alternatively, analysis computers can be grouped or clustered together in a centralized location. With this configuration, for example, a first imaging computer at a first location and a second imaging computer at a second location can share the cluster of analyzer computers.

In some embodiments, analyzer computers are configured so that electronic image data is processed during idle cycles of the analysis computers. In other embodiments, multiple analysis computers are configured to simultaneously process different portions of electronic image data of a single slide. In embodiments including or involving multiple analysis computers, the analysis computers can be heterogeneous. Further, imaging and analysis computers can operate on different platforms.

Other aspects and features of the embodiments will be evident from reading the following description of the embodiments.

BRIEF DESCRIPTION OF THE DRAWINGS

Referring now to the drawings in which like reference numbers represent corresponding parts throughout and in which.

DETAILED DESCRIPTION OF ILLUSTRATED EMBODIMENTS

Embodiments provide different architectures and systems and methods that advantageously separate image acquisition and image processing by removing the requirement for an analyzing computer to keep pace with an imager when imaging and biological specimens on a specimen carrier, such as a slide. These improvements are realized by eliminating the one-to-one correspondence between imagers and computers as is used in known systems. Rather than processing images while the slide is still on the stage, embodiments utilize more efficient systems and methods that cache gathered images in a temporary storage location accessible to dedicated analyzer computers located elsewhere on a network. The dedicated analyzer computers, rather than the imager computers, process image data from this image cache. Once finished, the analyzer computers write the results to a database and delete the images from the cache.

By decoupling image acquisition from image analysis, embodiments eliminate the need for a single, shared computer to perform both imaging and analysis processing. Further, embodiments advantageously provide improved flexibility and enable more advanced analysis algorithms to be utilized without compromising image acquisition. Additionally, embodiments provide improved flexibility in controlling system throughput, and a system can contain various numbers of analyzer computers as may be necessary to keep pace with the incoming stream of images from imaging computers.

Figure 1:
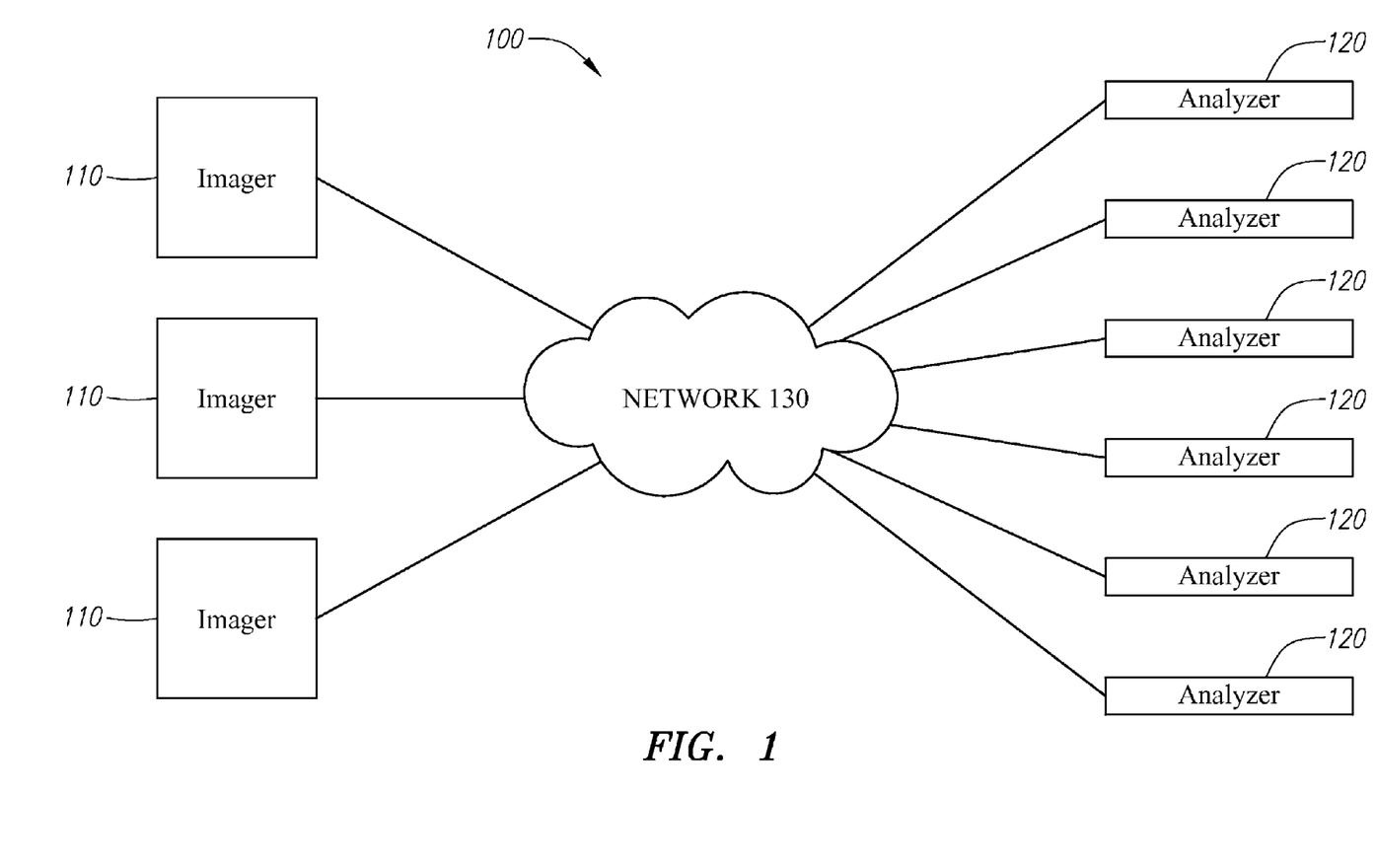
FIG. 1 illustrates a biological screening system constructed in accordance with one embodiment.

Referring to FIG. 1, a biological screening system 100 constructed in accordance with one embodiment includes one or more imaging computers, machines, devices or processors (generally "imagers" or "imaging computers") 110 and one or more analyzer computers, machines, devices or processors (generally "analyzers" or "analyzer computers") 120 connected to a network 130, such as a Local Area Network (LAN) or a Wide Area Network (WAN). An imager 110 and an analyzer 120 can be separated from each other and in different locations, e.g., in different locations within a laboratory or building or geographically separated from each other.

Each imager 110 is configured to acquire images of a specimen slide. However, with embodiments, imagers 110 are not required to process the images or electronic image data (generally "image data") 112. Rather, the image data 112 is sent over the network 130 to one or more analyzers 120, which are configured to filter and process the image data 112 for purposes of, for example, identifying particular areas or objects of interest and that may warrant further review by a cytotechnologist. The imagers 110 and analyzers 120 are configured and connected so that the process of acquiring images is separated from processing the image data 112, thereby relieving imagers 110 from image processing burdens.

According to one embodiment, the number of analyzers 120 is different than the number of imagers 110. For example, in the embodiment illustrated in FIG. 1, the number of analyzers 120 is greater than the number of imagers 110. According to one embodiment, the ratio of the number of analyzers 120 to the number of imagers 110 is at least 3:2. According to another embodiment, the ratio of the number of analyzers 120 to the number of imagers 110 is at least 2:1. Other ratios can be utilized as needed.

Example analyzer-to-imager ratios of 3:2 and 2:1, given today's personal computer speeds, allow overall system 100 throughput that is as fast as the imager 110 could gather the images, or roughly 2 minutes and 45 seconds per slide, which translates to about an 11.7 hour batch time for a full 250 slide batch. These processing speeds are significantly faster than the 3 minutes and 25 seconds per slide some known systems achieve, which translates to about a 14.25 hour batch time for a batch of 250 slides. Notably, a batch time of approximately 12 hours fits very nicely into a 24 hour workflow model, whereas a 14+ hour batch time, typically means that 10 of every 24 hours is non-productive. Other alternative embodiments can use different numbers of imagers 110 and analyzers 120 and ratios thereof as necessary to accommodate available processing times and desired processing speeds. The number of analyzers 120 relative to the number of imagers 110 may depend on, for example, the speed of image acquisition, the types of biological specimens being examined, the speed of the analyzers 120 and/or the extent to which analyzers 120 should keep pace with the imagers 110.

In one embodiment, a system 100 includes one imager 110 and multiple analyzer computers 120 that process electronic image data 112 for a single slide generated by the imager 110. According to another embodiment, multiple analyzers 120 simultaneously process different portions of the image data 112 of a single slide. In this manner, embodiments advantageously distribute image data 112 processing to multiple analyzers 120, thereby increasing the speed at which the image data 112 is processed and increasing the speed at which results 122 are generated. Further, with embodiments, multiple analyzers 120 can keep pace with the imager 110 as the imager generated image data 112 for each slide, thereby increasing the number of that can be processed in a given time and allowing rapid, real-time slide processing.

In alternative embodiments, the ratio of the number of the number of analyzers 120 to the number of imagers 110 can be less than one, e.g., 1:2. One example system configuration includes multiple imagers 110 feeding respective electronic image data 112 to a single analyzer 120. Such configurations may be suitable as computer processing speeds increase. Also, as yet another alternative, a single analyzer 120 (e.g., computer) may have multiple, separate processors or processing sub-systems that can be dedicated to different imagers 110. For purposes of explanation, this specification refers to a ratio of the number of analyzers 120 to the number of imagers 110 as being greater than one. Further advantages achieved with embodiments include the ability to use more sophisticated image processing algorithms without compromising image acquisition. Additionally, with these embodiments, it is not necessary to perform time-consuming and compromising optimization steps on the analysis algorithm that are otherwise required when working with a limited and fixed amount of computing resources. Instead, if image processing is 50% slower, additional analyzers 120 can be added to the network 130 to maintain system 100 throughput, thereby allowing image processing improvements to be rapidly deployed. It should be appreciated that having the flexibility to add significantly more processing power to the analyzer 120 also enables new processing opportunities that today are dismissed as being computationally impossible or infeasible considering the limited and shared computing resources that are used for image acquisition and processing.

Figure 2:
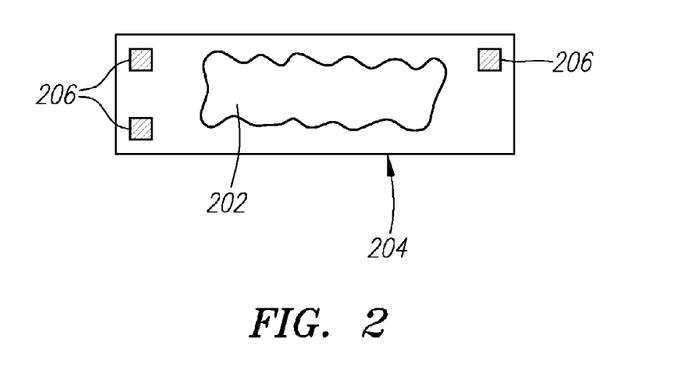
FIG. 2 is a plan view of a standard microscope slide carrying a biological specimen.
Figure 3:
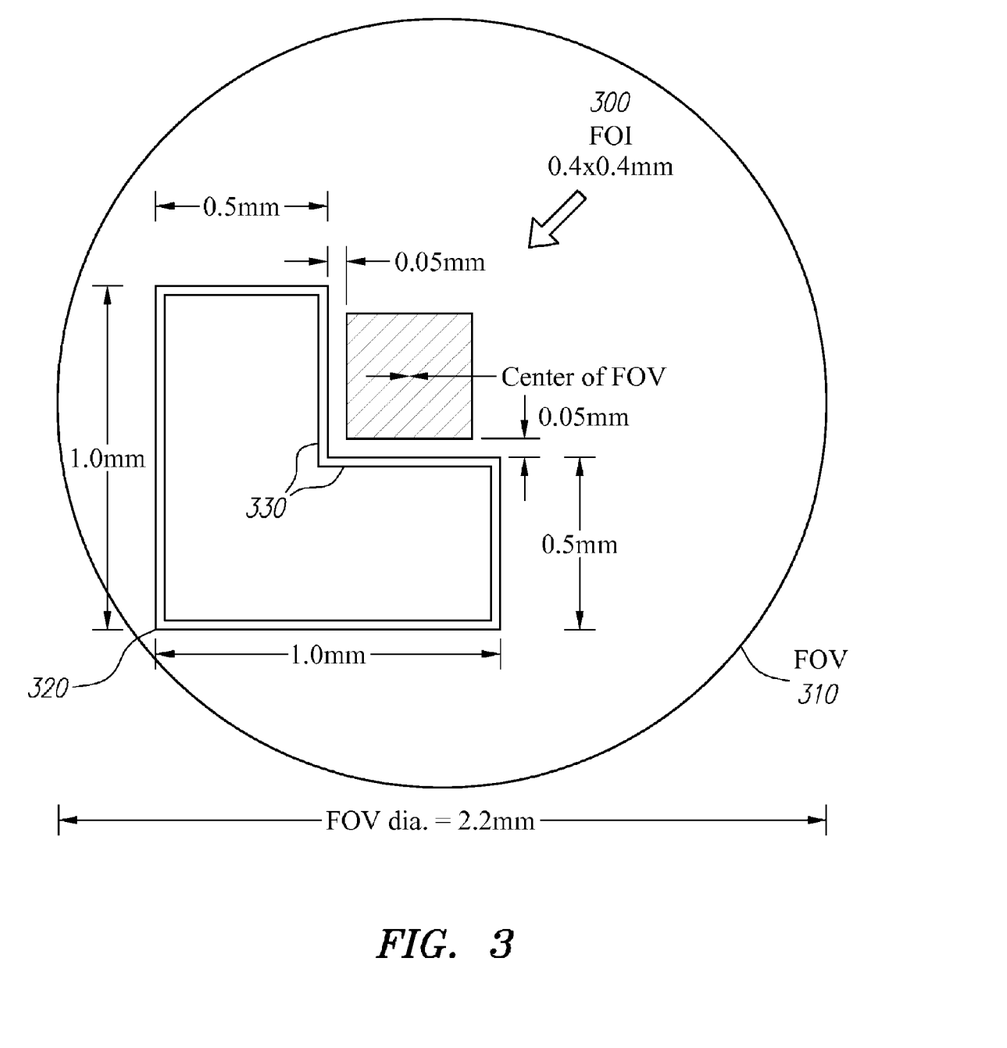
FIG. 3 is a view of a field of interest (FOI) and marker indicator as shown through a field of view (FOV) of a microscope.

Referring to FIGS. 2 and 3, the screening system 100 shown in FIG. 1 can be configured for presenting a biological specimen 202 located on a microscope slide 204. The biological specimen 202 is typically placed on the slide 204 as a thin cytological layer. Preferably, a cover slip (not shown) is adhered to the specimen 202, thereby fixing the specimen 202 in position on the slide 204. The specimen 202 may be stained with any suitable stain. Coordinates or locations of objects or areas of interest are identified relative to fiducial marks 206.

According to one embodiment, the system 100 can be used to image and process various types of biological specimens 202 (or even a non-biological specimen, such as a computer chip) that require further review. According to one embodiment, the system 100 is used for the presentation of cytological cervical or vaginal cellular material, such as that typically found on a Pap smear slide. In this embodiment, the specimen 202 may be stained with any suitable stain, such as a Papanicolaou stain, e.g., a ThinPrep® stain. Persons skilled in the art will appreciate that embodiments can be applied to other types of biological specimens.

Figure 4:
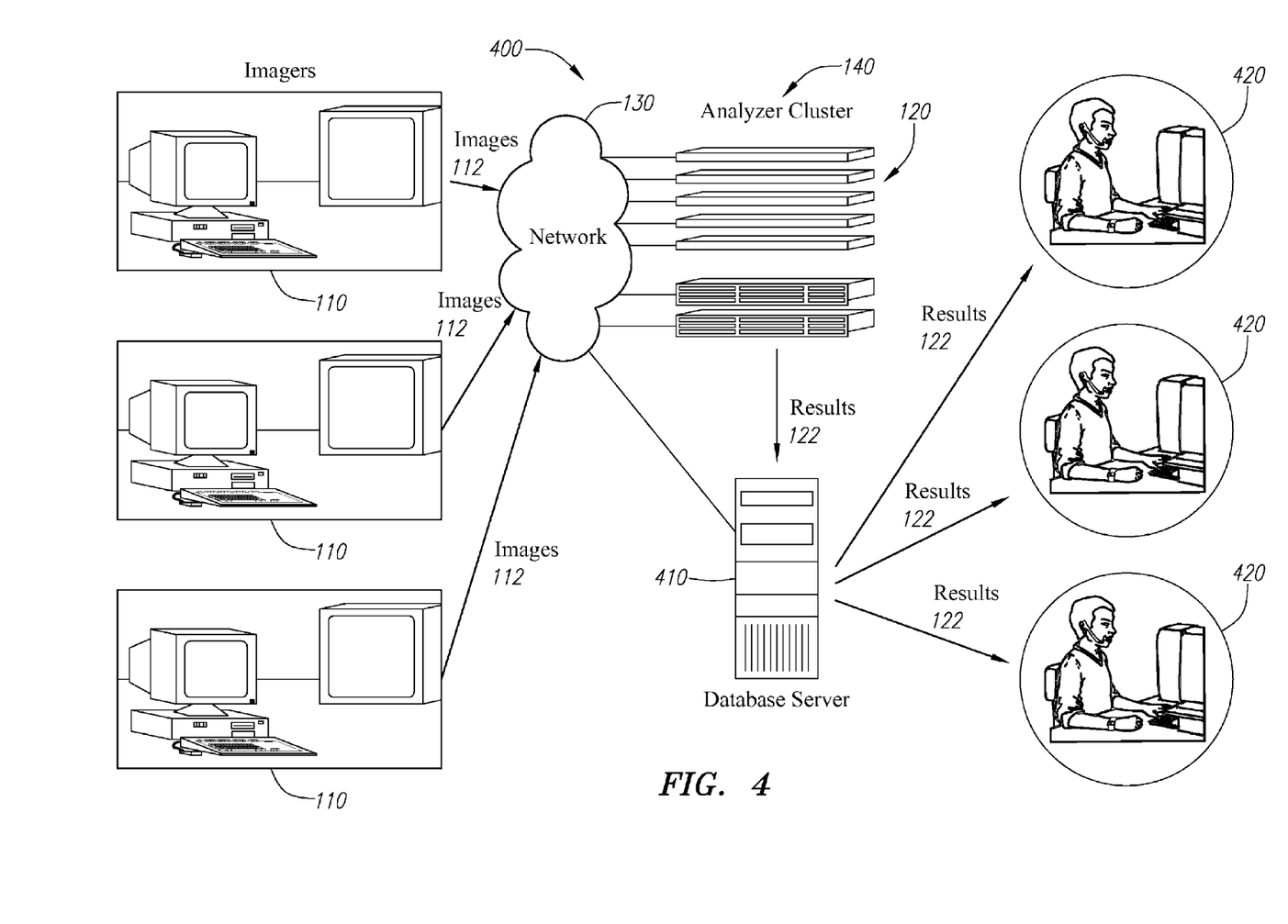
FIG. 4 illustrates a biological screening system constructed in accordance with one embodiment.
Figure 5:
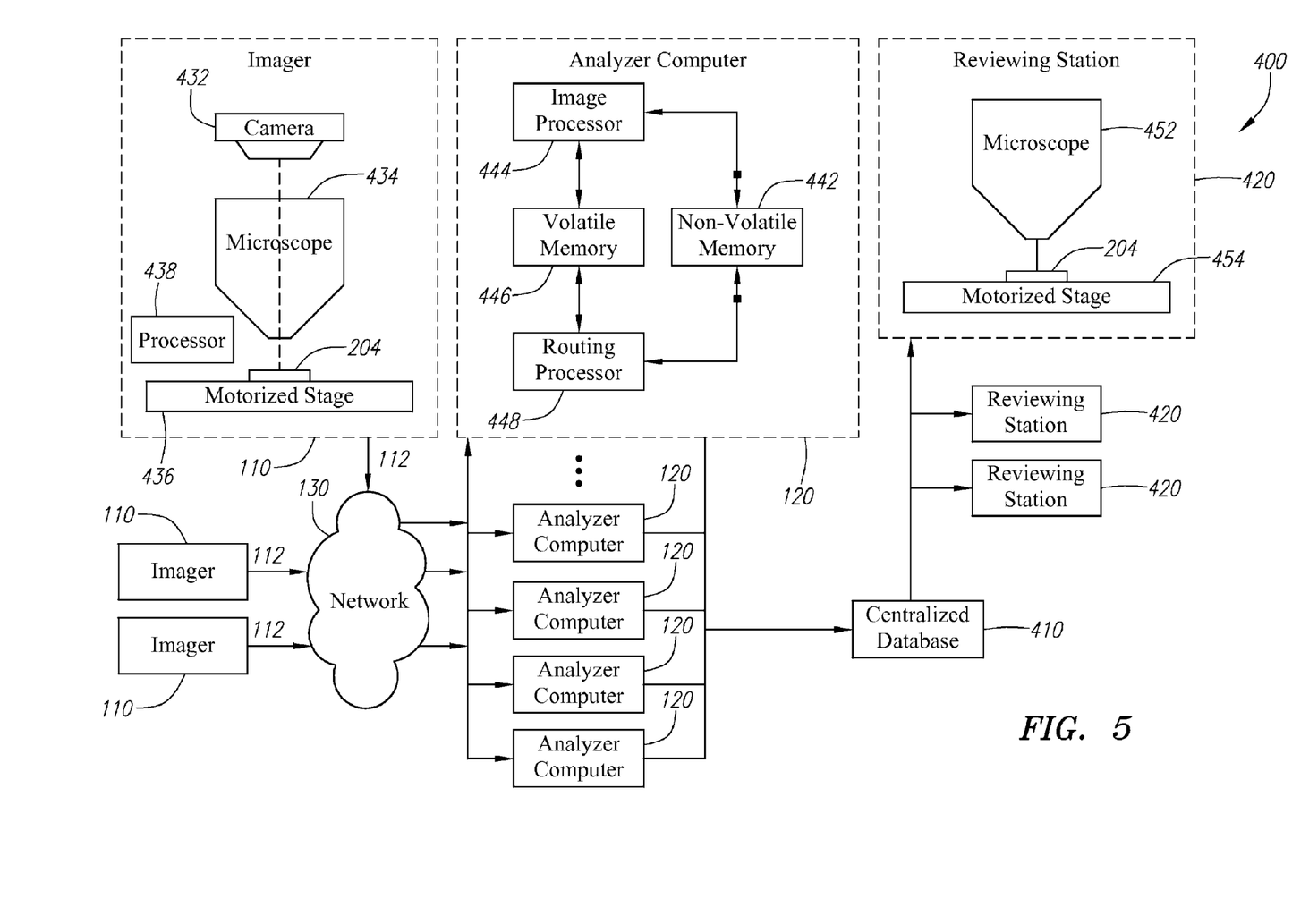
FIG. 5 is a block diagram of a biological screening system according to one embodiment.

Referring to FIG. 3, certain areas or objects of interest take the form of individual cells and cell clusters that are to be reviewed to check for the possible presence of an abnormal condition, such as malignancy or pre-malignancy. According to one embodiment, the system 100 is configured for presenting a biological specimen or material 202 located on the microscope slide 204 to a technician, such as a cytotechnologist, who can then review objects of interest (OOIs) located in the biological material 202. The OOIs are arranged in a number of Fields of Interest (FOI) 300 that cover portions of the slide 204 so that the cytotechnologist's attention can be subsequently focused on OOIs within the FOIs 300, rather than slide regions that are not pertinent. Further aspects of embodiments and how they are used to image and analyze specimen slides are described with reference to FIGS. 4 and 5. Referring to FIGS. 4 and 5, a system 400 according to another embodiment includes one or more imagers 110, e.g., a plurality of imagers 110 as shown in FIG. 4, a plurality of analyzers 120, a centralized database or data store 410 and one or more review stations, computers, machines, devices, processors, microscopes (generally "review stations") 420. In the illustrated embodiment, multiple analyzers 120 are grouped together in a cluster 140 of analyzers 120 in a centralized location. Analyzers 120 in a cluster 140 may also share one or more components, e.g., cache or processing components. The number of analyzers 120 in a cluster 140 can be different, e.g., greater than, the number of imagers 110. Thus, FIGS. 4 and 5 illustrate further examples of suitable numbers of imagers 110 and analyzers 120.

During use, the imagers 110 obtain images of the biological material 202 contained on the slide 200 and generate images or electronic image data 112. The image data 112 is provided to analyzers 120 for filtering and processing. The analyzers 120 filter and process the image data 112 to generate results 122, which can be the identity of OOIs. The processing results 122 are provided by the analyzers 120 to a central database or data store 410, which stores results 122 that can be accessed by review stations 420. Various analyzers 120 within an analyzer cluster 140 can each work on different parts of the same specimen slide. A separate application can collect the analysis results 122 from each analyzer computer 120 within the cluster 140. The results 122 from each analyzer 120 are consolidated and written to the database 410 or sent to the review station 420.

Each review station 420 provides a field of view (FOV) 310 (shown in FIG. 3) that is scanned relative to each OOI in order to present the OOIs within the FOI 300 for viewing by a cytotechnologist. The system 400 may also comprise a user interface (not shown), including a monitor, keyboard, and mouse (all not shown), so that the cytotechnologist can interact with the system 10.

Each imager 110 is configured to acquire images of the specimen slide, which is typically contained within a cassette (not shown), along with other slides. During the imaging process, the slides are removed from the respective cassettes, imaged, and then returned to the cassettes in a serial fashion. For example, the imager 110 can process up to 10 cassettes, each holding up to 25 slides.

In the illustrated embodiment, each imager 110 includes a camera 432, a microscope 434, and a motorized stage 436. The camera 432 captures magnified images of the slide 204 through the microscope 434. Each imager 110 also includes a processor in the form of a computer 438, e.g., a personal computer (PC). Because the computer 438 of the imager 110 does not have to perform analyzer or image processing functions, it is not necessary to use a powerful computer 438. Thus, embodiments provide more flexibility in terms of the type and cost of a computer 438 that is used for image acquisition. For example, a less expensive computer 438 with less processing power can be used compared to known systems.

The camera 432 of the imager 110 can be any one of a variety of conventional cameras, such as a charge coupled device (CCD) camera, which alone or in conjunction with other components, such as an analog-to-digital (A/D) converter, can produce a digital output of sufficient resolution to allow processing of the captured images, for example a digital image having a resolution of 640×480 pixels. Preferably, each pixel is converted into an eight-bit value (0 to 255) depending on its optical transmittance, with "00000000" being the assigned value for least amount of light passing through the pixel, and "11111111" being the assigned value for a greatest amount of light passing through the pixel. Persons skilled in the art will appreciate that various resolutions and pixel depths can be utilized.

The slide 204 is mounted on the motorized stage 436, which scans the slide 204 relative to the viewing region of the microscope 434, while the camera 432 captures images over various regions of the biological specimen 202. The shutter speed of the camera 432 is preferably relatively high, so that the scanning speed and/or number of images taken can be maximized. The motorized stage 436 keeps track of the x-y coordinates of the images as they are captured by the camera 432. For example, encoders (not shown) can be coupled to the respective motors of the motorized stage 436 in order to track the net distance traveled in the x- and y-directions during imaging. These coordinates are measured relative to the fiducial marks 206 affixed to the slide 204 (shown in FIG. 2). These fiducial marks 206 will also be used by the reviewing station 420 to ensure that x-y coordinates of the slide 204 during the review process can be correlated to x-y coordinates of the slide 204 obtained during the imaging process.

According to one embodiment, each analyzer 120 includes a memory, such as non-volatile memory 442, e.g., a hard disk drive or digital disk drive, which is configured for temporarily storing the image cache obtained from the imagers 110; an image processor 444 that is configured to identify, locate, and rank the OOIs within the cached images; a memory, preferably in the form of a volatile memory 446, such as random access memory (RAM), for storing at least the image currently being processed, OOI information, and any other information temporarily by the image processor 444. If necessary, a routing processor 448 may be used to map a routing path that the reviewing stations 420 will use to scan from one OOI to the next.

According to one embodiment, analyzers 120 can be a high performance personal computer. While the imager 110 typically will run on a Windows® platform, analyzers 120 or analyzers 120 of a cluster 140, because they are decoupled from the imagers 110, may operate on a different, non-Windows® platform. For example, computers used in the analyzer cluster 140 can be supercomputers, Linux boxes, Sun Solaris boxes, or hybrid boxes containing custom hardware or digital signal processing (DSP) accelerator boards. Allowing the analyzer computers 120 to be decoupled from imagers 110 allows a different, more optimal platform to be used for analyzing the image data 112.

The non-volatile memory 442 of the analyzer 120 has sufficient hard drive storage to accommodate the image cache. In one embodiment, the non-volatile memory 442 may take the form of a Redundant Array of Inexpensive Disks (RAID) shared within the analyzer cluster 140, which boosts both overall performance and reliability. Notably, off-the-shelf personal computers are equipped with Serial ATA (SATA) RAID options, so the use of RAID this is not a barrier, nor is it cost prohibitive.

In a typical system, each slide produces approximately 1 GB of image data. Since the idea is for the cluster of computers 120 to nominally keep up with the imagers 110, it is not necessary to cache a huge number of images. As a cassette (e.g., 25 slides) is processed, the resulting images 112 are cached within the non-volatile memory 442, but they are not analyzed until a verification slide is re-imaged after the 25 slides have been digitized. Thus, for each imager 110, the analyzer cluster 140 uses image cache space of 25×1 GB or 25 GB of storage. In the depicted example, the analyzer cluster 140 provides 3×25 GB or 75 GB of image cache space. This is, in today's terms, a small amount of low cost storage.

In the embodiment shown in FIGS. 4 and 5, three reviewing stations 420 are coupled to the central database 410, so that up to three cytotechnologists have simultaneous access to the pertinent results or information 122 generated by the analyzers 120 and stored in the database 410. Before discussing the details of the reviewing stations 420, reference is made again to FIG. 3, which illustrates an exemplary FOV 310 that each reviewing station 420 centers over a FOI 300. In the illustrated embodiment, the FOV 310 has a diameter of 2.2 mm, and the FOI 300 is defined by a 0.4 mm×0.4 mm square circumscribed by the FOV 310. In the actual embodiment, the borders of the FOI 300 are imaginary and cannot be seen, so that the cytotechnologist's view of any OOIs is not obstructed. In order to more quickly direct the cytotechnologist's attention to the FOI 300 and to provide a reference that generally indicates the exact region bound by the imaginary borders of the FOI 300, an L-shaped mark indicator 320 is provided.

The mark indicator 320 captures the FOI 300 (i.e., an open square portion 330 of the mark indicator 320 borders the left and bottom sides of the FOI 300). A 0.05 mm margin is provided between the mark indicator 320 borders and the imaginary borders of the FOI 300, so that the portions of OOIs extending outside of the left and bottom borders of the FOI 300 (resulting from an OOI that is included within the FOI 300, but centered near the left or bottom border of the FOI 300) will not be obstructed by the mark indicator 320. The mark indicator 320 also serves to provide a means for the cytotechnologist to electronically mark the FOI (e.g., by pushing a button that electronically colors the mark indicator 320) as requiring further review by a pathologist (e.g., if an OOI has malignant or pre-malignant attributes).

Referring to FIG. 5, each reviewing station 420 includes a microscope 452 and a motorized stage 454. The slide 204 (after image processing) is mounted on the motorized stage 454, which moves the slide 204 relative to the viewing region of the microscope 452 based on the routing plan and a transformation of the x-y coordinates of the FOIs 300 obtained from memory 442. Specifically, these x-y coordinates, which were acquired relative to the x-y coordinate system of the imager 110, will be transformed into the x-y coordinate system of the reviewing station 420 using the fiducial marks 206 affixed to the slide 204 (as shown in FIG. 3). Thus, it is ensured that the x-y coordinates of the slide 204 during the reviewing process are correlated to the x-y coordinates of the slide 204 during the imaging process. The motorized stage 454 will then move in accordance with the transformed x-y coordinates of the FOIs 300, as dictated by the routing plan.

In the illustrated embodiment, to advance from one FOI 300 to another, the cytotechnologist presses an activation switch (not shown). In this sense, the reviewing station 420 is semi-automatic. Alternatively, the FOIs 300 are automatically advanced from one to the next. In this case, the motorized stage 454 may optionally pause for a predetermined amount of time for each FOI 300. In this sense, the reviewing station 420 is fully automatic.

As the selected FOIs 300 are presented in the FOV 310 of the microscope 452, the cytotechnologist reviews the FOIs 300 and makes decisions about the level of cell abnormality, if any. The cytotechnologist will electronically mark any FOIs 300 that are suspect. The cytotechnologist is capable of returning to a previously viewed FOI 300 and manually moving to (and viewing) locations on the slide not encompassed by FOIs 300. Following review of the slide 204, if any FOIs 300 have been marked by the cytotechnologist, the reviewing station 420 preferably automatically scans the entire biological specimen 202, so that 100% viewing coverage is ensured. The cytotechnologist is able to pause the autoscan and move the stage 454 in order to reposition and access locations on the slide 204, as desired.

The network 130 can be a Local Area Network (LAN), Wide Area Network (WAN) or other suitable network. According to one embodiment, analyzers 120 or a cluster 140 of analyzers can be located remotely from the imagers, e.g., in a different geographic location. This would allow multiple imagers 110 from geographically distributed locations to share an analyzer cluster 140 in a centralized location via the network 130. Sharing a single analyzer cluster 140 also enables use more powerful computers in the cluster 140, since the cost of the more powerful computers would be spread across all of the imagers 110.

Gigabit Ethernet may also be used to reduce network 130 bottlenecks. Gigabit Ethernet may also be useful in large laboratories to segment the network 130 using switches to isolate some of the traffic. In such a configuration there might be multiple analyzer clusters 140 with imagers 110 distributed evenly across the cluster 140. Lossless compression (typically 2× ratios) may be used on the cached images, again to maximize the available network 130 and disk bandwidth. It is also possible to configure the analyzer cluster 140 as a load-balanced cluster, which would make the cluster 140 appear as one very fast machine to the imagers 110.

In an alternative embodiment, computationally expensive image data 112 processing can be distributed across a very large analyzer cluster 140. In one embodiment, processing can be distributed across different analyzers 120 of a cluster 140 using by basically harvesting the "spare" cycles of various analyzers 120. This approach is similar to the SETI-At-Home Project. In this model, personal computers on the Internet run a "screen-saver" application, which, when the personal computer is idle, pulls data from a known location on the network 130, analyzes it, and pushes the results back to the known location. At any given time, many personal computers on the network 130 are idle and are available to analyze data. Using this approach or other suitable approaches, it would be possible to distribute the image analysis across the analyzer cluster 140, using available spare cycles of one or more analyzers 120 of the cluster 140. In this case, the analyzer cluster 140 illustrated in FIG. 1 would be virtual. This technique, due to the large datasets, and due to the sensitive and confidential nature of the images may be implemented with appropriate modifications. One example implementation is analyzers 120 that are distributed within the laboratory and connected to a high-performance Local Area Network 130.

Further, the scalability of this system architecture allows the analyzer computers 120 to be shared among all the imagers 110 on the network 130, representing a potential cost savings. There are other secondary benefits of this approach. For example, the analyzers 120 can be heterogeneous since they are not coupled to the imager 110 and many of the requirements for the imager 110 are relaxed. This provides enhanced flexibility since as the system is upgraded, pre-existing analyzer 120 computers can be left in place and, if more capacity is needed, new higher performance machines can be added to the cluster 140 of analyzers 120.

Additionally, while analyzers 120 and analyzer clusters 140 are illustrated as analyzing image data 112 of Pap smear slides, it should be noted that embodiments can be used to analyze different kinds of slides. Different image analysis processing can be used on the same analyzer 120 or cluster 140 as appropriate for different types of digitized tissue samples. As images arrive from an imager 110, the type of processing that is required and the location to which results 122 are sent can be identified.

Although particular embodiments have been shown and described, it should be understood that the above description is not intended to limit the scope of embodiments since various changes and modifications may be made without departing from the scope of the claims. For example, persons skilled in the art will appreciate that embodiments can be applied to various biological specimens. Further, systems can utilize various numbers of imagers, analyzers, analyzer clusters, databases and review stations. Image data from one imager can be processed by multiple analyzers or a centralized cluster of analyzers. Additionally, image data from multiple images can be processed by the same analyzer, multiple analyzers, or a centralized cluster of analyzers. Thus, embodiments are intended to cover alternatives, modifications, and equivalents that fall within the scope of the claims.

What is claimed is:

1. A system for imaging and analyzing a biological specimen on a specimen carrier, comprising:

at least one imaging computer configured to acquire images of a biological specimen on a specimen carrier and generate electronic image data from the images;

at least one analysis computer connected to the at least one imaging computer through a network and being configured to process the electronic image data and generate results of the electronic image data processing, wherein the number of analysis computers is different than the number of imaging computers; and at least one review station in electronic communication with a database storing the results of the electronic image data processing, wherein the at least one review station and the at least one analysis computer are physically separate components, and wherein the at least one imaging computer and the at least one review station each comprise a stage for holding the specimen carrier.

2. The system of claim 1, wherein the database is coupled to each of the at least one analysis computers; and wherein each analysis computer is configured to transmit their respective processing results to the database, and each review station is capable of accessing the stored results.

3. The system of claim 1, wherein the network is a Local Area Network or a Wide Area Network.

4. The system of claim 1 comprising one imaging computer and a plurality of analysis computers.

5. The system of claim 1 comprising a plurality of imaging computers and a plurality of analysis computers.

6. The system 1, wherein the number of analysis computers is greater than the number of imaging computers.

7. The system of claim 6, wherein the ratio of the number of analysis computers to the number of imaging computers is at least 3:2.

8. The system of claim 1 comprising a cluster of multiple analysis computers in a centralized location.

9. The system of claim 8 comprising first and second imaging computers, wherein a first imaging computer at a first location and a second imaging computer at a second location share the cluster of analysis computers.

10. The system of claim 8, wherein the cluster is configured so that electronic image data is processed during idle cycles of the analysis computers.

11. The system of claim 1 comprising multiple analysis computers configured to simultaneously process different portions of electronic image data of a single slide.

12. The system of claim 1, wherein each analysis computer is configured to identify Objects of Interest (OOIs) within the biological specimen.

13. The system of claim 1, wherein the at least one imaging computer and the at least one analysis computer operate on different platforms.

14. The system of claim 1 comprising a plurality of heterogeneous analysis computers.

15. The system of claim 1, wherein the at least one analysis computer is located remotely from the at least one imaging computer.

16. A system for imaging and analyzing a biological specimen on a specimen carrier, comprising:

at least one imaging computer configured to acquire images of a biological specimen on a specimen carrier and generate electronic image data from the images;

a plurality of analysis computers connected to the at least one imaging computer through a network and being configured to process the electronic image data, wherein the number of analysis computers is greater than the number of imaging computers;

a database configured to store results generated by the plurality of analysis computers; and one or more review stations capable of accessing the stored results, wherein the one or more review stations and the plurality of analysis computers are physically separate components.

17. The system of claim 16, wherein the network is a Local Area Network or a Wide Area Network.

18. The system of claim 16 comprising a cluster of multiple analysis computers in a centralized location.

19. The system of claim 16, wherein multiple analysis computers are configured to simultaneously process different portions of electronic image data of a single slide.

20. The system of claim 16, wherein the analysis computers are located remotely from the at least one imaging computer.

21. A method of imaging and analyzing a biological specimen on a specimen carrier, comprising:

acquiring images of a biological specimen on a specimen carrier using at least one imaging computer;

generating electronic image data from the acquired images;

transmitting the electronic image data from the at least one imaging computer over a network to at least one analysis computer, wherein the number of analysis computers is different than the number of imaging computers;

processing the electronic image data using the at least one analysis computer, thereby generating results of the electronic image data processing;

storing the results of the electronic image data processing to a database; and accessing the database using at least one review station, wherein the at least one review station and the at least one analysis computer are physically separate components.

22. The method of claim 21, wherein the transmitting further comprises transmitting the electronic image data from one imaging computer to multiple analysis computers.

23. The method of claim 21, wherein processing the electronic image data further comprises processing the electronic image data to identify Objects of Interest (OOIs) in the biological specimen.

24. The method of claim 21, wherein processing the electronic image data is performed remotely from the at least one imaging computer.

25. The method of claim 21, wherein processing the electronic image data further comprises simultaneously processing different portions of the electronic image data of a single slide using multiple analysis computers.

26. A method of imaging and analyzing a biological specimen on a specimen carrier, comprising:

acquiring images of a biological specimen on a specimen carrier using one or more imaging computers;

generating electronic image data from the acquired images;

transmitting the electronic image data from the one or more imaging computers over a network to one or more of a plurality of analysis computers, wherein the number of analysis computers is greater than the number of imaging computers;

processing the electronic image data using the one or more of the plurality of analysis computers;

storing the result of processing the electronic image data to a database; and accessing the database using a plurality of review stations, wherein the plurality of review stations and the plurality of analysis computers are physically separate components.

27. The method of claim 26, wherein processing the electronic image data further comprises simultaneously processing different portions of the electronic image data of a single slide using multiple analysis computers.

28. The system of claim 1, wherein the at least one review station is located remotely from the at least one analysis computer.

29. The system of claim 1, wherein the at least one imaging computer and the at least one analysis computer are not capable of accessing the results stored in the database.

* * * * *